Figure 1:
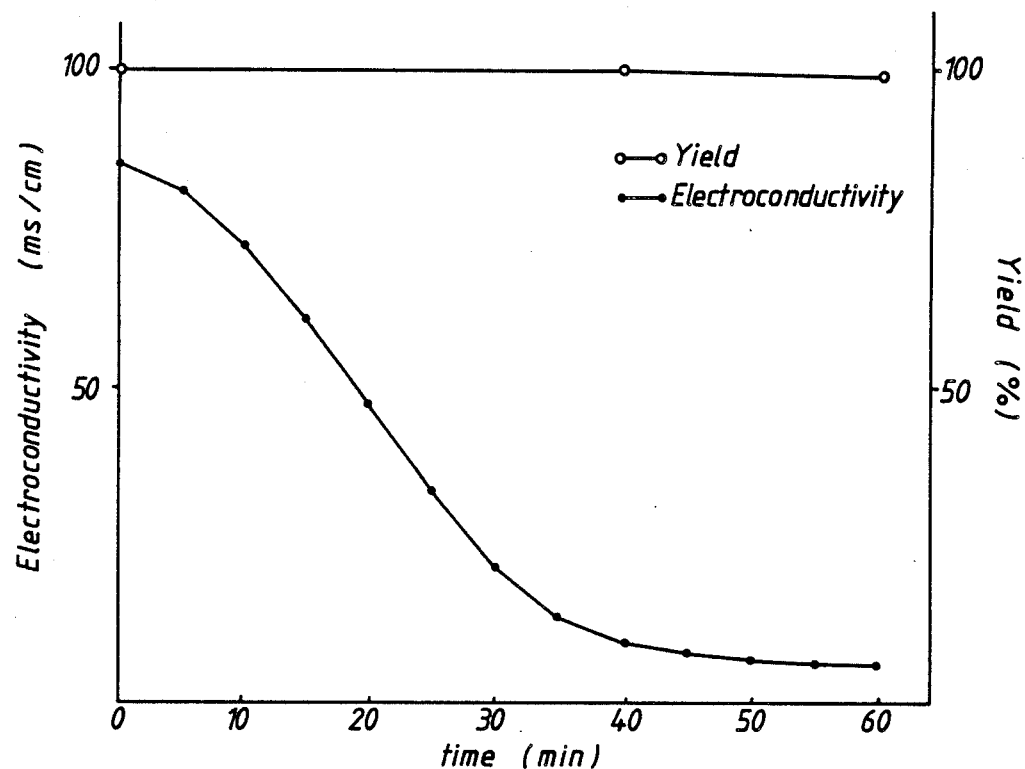

United States Patent [19]
Umeda et al.

[11] Patent Number: 4,981,595
[45] Date of Patent: Jan. 1, 1991

[54] PROCESS FOR THE PURIFICATION OF SPERGUALIN-RELATED COMPOUNDS

[75] Inventors: Yoshihisa Umeda, Otsu; Makoto Moriguchi, Jyoyo; Keiko Miyazaki, Takatsuki; Toru Kurome, Otsu; Ikunoshin Kato, Uji; Tetsushi Saino, Yono, all of Japan

[73] Assignees: Takara Shuzo Co., Ltd., Kyoto; Nippon Kayaku Kabushiki Kaisha, Tokyo, both of Japan

[21] Appl. No.: 370,746

[22] Filed: Jun. 20, 1989

[30] Foreign Application Priority Data

Jul. 1, 1988 [JP] Japan .................... 63-164153

[51] Int. Cl.$^5$ .................. B01D 61/02; B01D 61/42
[52] U.S. Cl. .................... 210/644; 210/651; 210/806; 204/182.6
[58] Field of Search ............... 210/644, 645, 651, 652, 210/638, 806; 514/620, 626, 908, 885; 260/404.5; 549/419; 548/342, 504, 538; 564/157, 159, 201; 204/182.6, 186

[56] References Cited

U.S. PATENT DOCUMENTS

| | | | |
|---|---|---|---|
| 3,932,374 | 1/1976 | Umezawa et al. | 530/322 |
| 3,992,524 | 11/1976 | Umezawa et al. | 435/71.3 |
| 4,416,899 | 11/1983 | Umezawa et al. | 424/320 |
| 4,518,532 | 5/1985 | Umezawa et al. | 260/404.5 |
| 4,518,802 | 5/1985 | Umezawa et al. | 564/201 |
| 4,525,299 | 6/1985 | Umezawa et al. | 564/159 |
| 4,529,549 | 7/1985 | Umezawa et al. | 548/342 |
| 4,556,735 | 12/1985 | Umezawa et al. | 564/157 |
| 4,603,015 | 7/1986 | Umeda et al. | 564/201 |
| 4,658,058 | 4/1987 | Umezawa et al. | 564/159 |
| 4,851,446 | 7/1989 | Umezawa | 514/620 |

Primary Examiner—W. Gary Jones
Attorney, Agent, or Firm—Wenderoth, Lind & Ponack

[57] ABSTRACT

Process for purifying spergualin-related compounds and their synthetic intermediates, by subjecting a solution containing such spergualin-related compounds or intermediates to electrodialysis and/or reverse osmosis.

1 Claim, 1 Drawing Sheet

PROCESS FOR THE PURIFICATION OF SPERGUALIN-RELATED COMPOUNDS

The present invention relates to a novel method for the purification of spergualin-related compounds which are useful as antitumor substances or immunosuppressive substances, and of their synthetic intermediates.

Spergualin is a antitumor antibiotic discovered by H. Umezawa et al (Japanese Patent Kokai No. 48957/82), and many derivatives and analogues of spergualin have been reported (Japanese Pat. Kokai No. 62152/83, No. 42356/84, No. 185758/85, and No. 48660/87). In addition, the immunosuppressive activity of spergualin and its related compounds has been reported (Japanese Patent Kokai No. 129119/86). These spergualin-related compounds are produced by means of cultivation, semi-synthesis, or total synthesis.

Among spergualin, its derivatives, and its analogues (hereinafter referred to as spergualin-related compounds), spergualin and 15-deoxyspergualin, which have excellent biological activity are relatively unstable and so it has been extremely difficult to produce a large amount of them with high quality. That is, spergualin-related compounds, their synthetic intermediate, glyoxylylspermidine, and their derivatives readily decompose during concentration by being heated during the purification process. For example, there is problem in the process of removing inorganic salt from the active fractions and/or of concentrating the fractions containing spergualin-related compounds that are eluted from an ion-exchange resin column and/or porous absorbent resin column by use of an aqueous solution of inorganic salt. In the processes of concentration and desalination, concentration by freeze-drying, and extraction with organic solvent have been unavoidable steps, because other processes suitable for spergualin-related compounds were not available. Thus, in order to help prevent degradation, the concentration step had to be done at low temperature with a small portion or by freeze-drying, which reduces productivity. A production process that includes such concentration step is not usable for industrial-scale production. Moreover, the former processes of concentration and/or desalination were not applicable to large-scale production, and so some effective and economical methods have been needed.

The object of the present invention is to provide a process for the purification of spergualin-related compounds and their synthetic intermediates by means of desalination and/or concentration processes which are practicable in industrial production.

Briefly, this invention relates to a process for the purification of spergualin-related compounds and their synthetic intermediates by means of electrodialysis and/or reverse osmosis.

As a result of intensive studies about desalination, the inventors of the present invention have found that desalination can effectively be achieved by electrodialysis of a solution containing spergualin-related compounds and inorganic salt, or a solution containing their synthetic intermediates. As well as salts, acids or bases can be removed by electrodialysis if desired. It has also been found that compounds with low molecular weight such as spergualin-related compounds and their synthetic intermediates, which have positively charged functional groups such as amino or guanidino groups, can be recovered in an extremely high yield. In addition, as a result of thorough studies about the concentration of a solution containing spergualin-related compounds and their intermediates, the inventors have found that concentration can effectively be achieved by reverse osmosis, during which degradation of spergualin-related compounds and their intermediates is greatly decreased. Also, recovery of compounds with low molecular weight, such as spergualin-related compounds and their intermediates, is extremely high. In this way, the inventors completed the present invention.

Typical examples of spergualin-related compounds have the general formula:

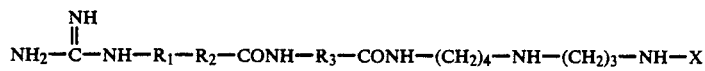

wherein $R_1$ is $-(CH_2)_4-$, $-(CH_2)_6-$,

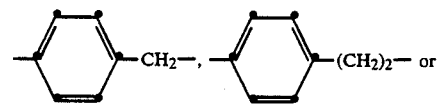

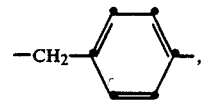

$R_2$ is $-(CH_2)_2-$, $-CH(OH)CH_2-$ or $-CH=CH-$, $R_3$ is $-CH(OH)-$, $-CH(OCH_3)-$, $-CH_2-$ or $-CH(CH_2OH)-$, and X is hydrogen or an amino acid or peptide wherein the hydroxy group of a carboxyl group has been removed, and pharmaceutically acceptable salts thereof.

As more specific examples there may be mentioned the following compounds:
(1) N-[4-(3-aminopropyl)aminobutyl]-2-(7-guanidino-heptanamide)-2-hydroxyethanamide (15-deoxyspergualin)
(2) N-[4-(3-aminopropyl)aminobutyl]-2-(7-guanidino-heptanamide)-2-methoxyethanamide
(3) N-[4-(3-aminopropyl)aminobutyl]-2-(9-guanidino-nonanamide-2-hydroxyethanamide
(4) N-[4-(3-aminopropyl)aminobutyl]-2-(7-guanidino-heptanamide)-ethanamide
(5) N-[4-(3-aminopropyl)aminobutyl]-2-(7-guanidino-heptanamide)-(S)-2-hydroxymethylethanamide
(6) N-[4-(3-aminopropyl)aminobutyl]-2-[4-(p-guanidinophenyl)-butan amide]-ethanamide
(7) N-[4-(3-aminopropyl)aminobutyl]-2-[4-(p-guanidinophenyl)-butan amide]-(S)-2-hydroxymethylethanamide
(8) N-[4-(3-aminopropyl)aminobutyl]-2-[3-(p-guanidinomethylphenyl)-propanamide]-(S)-2-hydroxymethylethanamide
(9) N-[4-(3-aminopropyl)aminobutyl]-2-[3-(p-guanidinophenyl)-pentanamide]-(S)-2-hydroxymethylethanamide
(10) N-[4-(3-aminopropyl)aminobutyl]-2-(7-guanidino-hept-2enamide)-2-methoxyethanamide
(11) N-[4-(3-aminopropyl)aminobutyl]-2-(9-guanidino-nona-2enamide)-2-hydroxyethanamide
(12) spergualin

(13) N-[[4-[3-((D,L,DL)-phenylglycyl)aminopropyl-]aminobutyl]]-2-(7-guanidinoheptanamide)-(S)-2-hydroxymethylethanamide

(14) N-[[4-[3-((L)-leucyl-(L)-leucyl)aminopropyl-]aminobutyl]]-2-(7-guanidinoheptanamide)-(S)-2-hydroxymethylethanamide These compounds have the chemical structures shown in Table 1.

change and/or porous absorbent resin column chromatography with use of a solution with inorganic salt (for example, sodium chloride) as the solution for elution to remove impurities and by-products.

The concentration of spergualin-related compounds and/or their synthetic intermediates in the solution is usually in the range of from 0.1 to 10% by weight, and that of the salt is in the range of from 0.1 to 10% by

TABLE 1

$$NH_2-\overset{\overset{NH}{\|}}{C}-NH-R_1-R_2-CONH-R_3-CONH-(CH_2)_4-NH-(CH_2)_3-NH-X$$

| Compound No. | $R_1$ | $R_2$ | $R_3$ | X |
|---|---|---|---|---|
| (1) | $-(CH_2)_4-$ | $-(CH_2)_2-$ | $-CH(OH)-$ | H |
| (2) | " | " | $-CH(OCH_3)-$ | " |
| (3) | $-(CH_2)_6-$ | " | $-CH(OH)-$ | " |
| (4) | $-(CH_2)_4-$ | " | $-CH_2-$ | " |
| (5) | " | " | (S) $-CH(CH_2OH)-$ | " |
| (6) | 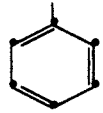 | " | $-CH_2-$ | " |
| (7) | " | " | (S) $-CH(CH_2OH)-$ | " |
| (8) | 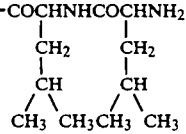 | " | " | " |
| (9) | 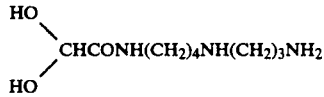 | $-(CH_2)_2-$ | (S) $-(CH(CH_2OH)-$ | H |
| (10) | $-(CH_2)_4-$ | $-CH=CH-$ | $-CH(OCH_3)-$ | " |
| (11) | $-(CH_2)_6-$ | " | $-CH(OH)-$ | " |
| (12) | $-(CH_2)_4-$ | $-CH(OH)-CH_2-$ | " | " |
| (13) | " | $-(CH_2)_2-$ | (S) $-CH(CH_2OH)-$ | (D,L,DL) $-COCHNH_2$ attached to phenyl |
| (14) | " | " | " | (L,L) $-COCHNHCOCHNH_2$ with $CH_2$/$CH_2$, $CH$/$CH$, $CH_3$ $CH_3CH_3$ $CH_3$ |

Examples of a synthetic intermediate of spergualin-related compounds are glyoxylylspermidine of the following formula:

$$\underset{HO}{\overset{HO}{\diagdown}}CHCONH(CH_2)_4NH(CH_2)_3NH_2$$

and its derivatives.

Spergualin-related compounds and their synthetic intermediates mentioned above may be produced by methods described in Japanese Pat. Kokai No. 62152/83, No. 42356/84, No. 185758/85 and No. 48660/87. A solution containing a product obtained by the above mentioned processes is purified by ion exchange and/or porous absorbent resin column chromatography with use of a solution with inorganic salt (for example, sodium chloride) as the solution for elution to remove impurities and by-products.

weight, which can be chosen freely. Such solution is obtained from the column chromatography by use of various ion-exchange resins or porous absorbent resins. With regard to the ion-exchange resins, cation-exchange resins such as CM-Sephadex, Diaion SK-resins, and Diaion WK-resins may be exemplified. As the absorbent resins the Diaion HP series and Sepabeads SP series are among the examples.

According to the present invention, the solution is desalted and/or concentrated by means of electrodialysis and/or reverse osmosis.

The principle of electrodialysis is as follows. A continuous current is made to pass through alternating layers consisting of a cation-exchange membrane which has a negative charge such as that of a sulfonyl or carboxyl group, and an anionexchange membrane which has a positive charge such as that of a quaternary ammonium base or amino group. The driving force of electrodialysis is the potential difference between the electrodes at the two terminals. The electric charge on the membranes interferes or facilitates the movement of the ions being so treated. That is, cations penetrate through the cation-exchange membrane, which has a negative charge, but anions can not penetrate through the cation-exchange membrane, because they are repelled by the negative charge. However, the opposite is the case for the anion-exchange membrane, which has a positive charge, so that cations cannot penetrate through the anionexchange membrane, but anions can penetrate through the membrane. These different ion-exchange membranes thus have selective effects on ions which have opposite charges. For example, when sodium chloride is treated by electrodialysis, desalination occurs when the sodium ions pass through the ion-exchange membrane and move to the negative pole, while the chlorine ion passes through the ion-exchange membrane and moves to the positive electrode.

The ion-exchange membrane for the electrodialysis to be used in the purification of spergualin-related compounds and their synthetic intermediates according to the present invention has the qualities described above, and can be used only under the following necessary conditions. It is necessary to prevent the dialysis of substances which have positive functional groups such as amino groups, guanidino groups, or the like, and which have the relatively low molecular weights (about 1000 or less) of spergualin-related compounds and their synthetic intermediates, and it is necessary to dialyze selectively only the dissociated ions of the salts which are desired to be removed.

Ion-exchange membranes having these properties are called membranes for selective dialysis or permselective membranes. Recently, a variety of ion-exchange membranes which have permselectivity for ions of the same charge have been developed. A number of methods have been proposed to impart the ability of ion permselectivity to membranes. To classify them roughly, there is (1) increasing the degree of cross-linking, resulting in a dense structure, and (2) the induction of an opposite charge on the surface. That is, by adjustment of the size of the pores in the membrane, it is possible to regulate the permeation of the substances being treated according to differences in their molecular weight. Or, by the provision of a thin layer with a charge opposite to that of the main body of the ion-exchange membrane on the surface of the membrane, it is possible to select between ions with mono- and di-valence. Also, such a thin layer acts to increase the recovery of charged organic compounds of low molecular weight.

Ion-exchange membranes which can be used in the purification of spergualin-related compounds and their synthetic intermediates according to this invention are widely known; for example, it is possible to use any of the membranes listed in Table 2, which are quoted from page 216 of *Recent Membrane Techniques and their Applications*, published August 1984 (in Japanese) by the Fuji Techo System Co., Ltd., with the membrane being selected according to its intended use. Based on the principles described above, ion-exchange membranes for which selectivity has been increased by surface treatment are particularly desirable. The reason is that because of the positive charge of either the amino group or the guanidino group of the spergualin-related compounds or their synthetic intermediates, these compounds generally adsorb onto the membrane, and the phenomenon of breakthrough into the outer solution takes place; surface treatment is for the purpose of preventing the effectiveness of the desalination from declining, and to avoid decreases in the recovery. As a particularly suitable combination of ion-exchange membranes, there is, for example, the Asiplex [phonetic]cartridge AC-110 of the Asahi Chemical Industry Co., Ltd., but there is no particular limitation on what may be used, and to achieve the purpose of this invention, it is possible to use products that are based on such ion-exchange membranes and that have increased capacity, that have been modified, or that have been reconstructed.

TABLE 2

| Firm | Trademark | Kind | (Note 1) Exchange capacity (meq/g) | (Note 3) Water content (%) | Elec. resistance ($\Omega \cdot cm^2$) | Transport ratio | Thickness (mm) | Strength against breakage ($kg/cm^2$) |
| --- | --- | --- | --- | --- | --- | --- | --- | --- |
| Asahi Glass Co., Ltd. | Selemion ®  | | | | (Note 4) | (Note 8) | | |
| | CMV/CMR | Cation exchange | 1.5~1.8 | 15~16 | 2.0~3.5 | >0.92 | 0.13~0.15 | 3~5 |
| | AMV/AMR | Anion exchange | 2.0~2.3 | 15~16 | 1.5~3.0 | >0.94 | 0.11~0.15 | 3~5 |
| | ASV/ASR | " | 2.0~2.3 | 15~16 | 2.3~3.5 | >0.95 | 0.13~0.15 | 2~5 |
| | DMV/DSV | (for diffusion dialysis) | — | — | — | — | 0.13~0.17 | 3~5 |
| Asahi Chemical Industry Co., Ltd. | Asiplex ® | | | | (Note 5) | (Note 9) | | (Note 11) |
| | K-101 | Cation exchange | 2.8 | 38 | 4.0 | 0.91 | 0.21 | 3.2 |
| | A-101 | Anion exchange | 1.5 | 24 | 2.1 | 0.98 | 0.21 | 3.2 |
| Ionic Inc. | Nepton ® | | (Note 2) | | (Note 6) | (Note 10) | | |
| | CR61 AZL-386 | Cation exchange | 2.7 | 46 | 11 | 0.92 | 0.6 | 8 |
| | CR61-CZL-386 | " | 2.7 | 40 | 11 | 0.94 | 0.6 | 8 |
| | CR61-AZL-389 | " | 2.6 | 48 | — | 0.92 | 1.2 | 27 |
| | AR103 PZL-386 | Anion exchange | 1.8 | 46 | 12 | 0.95 | 0.6 | 10 |
| | AR103 QZL-386 | " | 2.1 | 36 | 9 | 0.97 | 0.63 | 10.8 |
| | AR103 PZL-389 | " | 1.6 | 43 | — | 0.95 | 1.4 | 25 |
| | AR204 SXZL-389 | " | 2.35 | 45 | 10 | 0.96 | 0.6 | 10 |
| Mitsubishi Petrochemical Co., Ltd. | Unilex ® | | | | (Note 4) | (Note 9) | | (Note 11) |
| | XYC-30 | Cation exchange | 2.0~2.5 | 28~35 | 6.0~8.0 | >0.9 | 0.40 ± 0.03 | 60~100 |
| | XYA-51 | Anion exchange | 1.0~2.0 | 35~40 | 4.0~6.0 | >0.9 | 0.40 ± 0.03 | 50~80 |
| Tokuyama Soda Co., Ltd. | Neosepta ® | | | | (Note 4) | (Note 7) | | |
| | CH-45T | Cation exchange | 1.8~2.3 | 25~35 | 1.8~2.5 | >0.98 | 0.15~0.17 | 3~5 |
| | C66-5T | " | 2.2~2.6 | 35~45 | 1.1~1.7 | >0.98 | 0.13~0.18 | 2~4 |
| | ACH-45T | Anion exchange | 1.3~2.0 | 20~35 | 2.0~2.7 | >0.98 | 0.14~0.20 | 4~6 |

TABLE 2-continued

| | | | Major ion-exchange membranes and their properties (No. 1) | | | | | |
|---|---|---|---|---|---|---|---|---|
| Firm | Trademark | Kind | (Note 1) Exchange capacity (meq/g) | (Note 3) Water content (%) | Elec. resistance (Ω · cm²) | Transport ratio | Thickness (mm) | Strength against breakage (kg/cm²) |
| | ACS | " | 1.5~2.2 | 20~30 | 2.0~2.5 | >0.98 | 0.14~0.20 | 4~6 |
| | AFN | (for diffusion dialysis) | — | — | — | — | 0.15~0.20 | 5~7 |

Note:
1. Exchange capacity per unit dry membrane
2. Exchange capacity per unit dry resin
3. Water content of unit of dry membrane
4. In 0.5N—NaCl
5. In 0.5N—Sea water
6. In 0.1N—NaCl
7. By electrophoresis in 0.5N—NaCl solution
8. With membrane potention of 0.5N—NaCl/1.0N—NaCl
9. With membrane potention of 0.5N—NaCl/0.25N—NaCl
10. By electrophoresis in 0.1N—NaCl solution
11. Strength when stretched It is possible to use any of the various kinds of electrodialysis apparatus that are commercially available in the electrodialysis done in this way. For example, very satisfactory results can be obtained by the use of an electrodialysis apparatus equipped with ion-exchange membranes of the AC-110 type from Asahi Chemical Industry Co., Ltd., with very little breakthrough of the spergualin-related compounds or their synthetic intermediates into the outer solution, and with removal of inorganic salts. As a rule, the desalination capacity of an electrodialysis device is governed by the surface area of the ion-exchange membrane; in this invention as well, the apparatus is to be used with ion-exchange membranes having a surface area suited to the scale of the planned use.

Examples of the salts which can be removed include sodium chloride, potassium chloride, lithium chloride, calcium chloride, magnesium chloride, potassium bromide, sodium bromide, lithium bromide, calcium bromide, magnesium bromide, potassium acetate, sodium acetate, lithium acetate, calcium acetate, magnesium acetate, potassium formate, sodium formate, lithium formate, calcium formate, magnesium formate, potassium carbonate, sodium carbonate, lithium carbonate, calcium carbonate, magnesium carbonate, potassium phosphate, sodium phosphate, lithium phosphate, calcium phosphate, magnesium phosphate, potassium sulfate, sodium sulfate, lithium sulfate, calcium sulfate, magnesium sulfate, and the like.

Examples of the acids and bases which can be removed include hydrochloric acid, hydrobromic acid, acetic acid, formic acid, carbonic acid, phosphoric acids, sulfuric acid etc., as well as potassium hydroxide, sodium hydroxide, lithium hydroxide, magnesium hydroxide, calcium hydroxide, etc.

The principles of the reverse osmosis process to be used in this invention are as follows. A semipermeable membrane, which can be penetrated by a solvent (usually water) but not by the solute, is used. Pressure is applied to the solution in opposition to the osmotic pressure, which promotes permeation in the direction opposite to that in which the solvent would generally move, giving rise to reverse osmosis, by which means the solute and the solvent can be separated. The driving force in reverse osmosis is the difference in pressure.

This semipermeable membrane is also called a membrane for reverse osmosis, and it is generally made of natural high molecular cellulose acetate or synthetic high molecular weight substance. As the raw material for the synthetic macromolecule, there may be used polyether amide, polyether urea, aromatic polyamide, sulfonated polyfurfuryl alcohol, polybenzimidazole, polypiperazine amide, sulfonated polysulfone, sulfonated phenylene oxide, polyethyleneiminetoluenediisocyanate, polyethyleneimine-acid chloride, polyamide carbonate, polybenzimidazolone, polyimide, polyether, denatured polyacrylonitrile, polyethyleneimine, etc. As such semipermeable membranes, flat-membranes, spirals, tubes, and hollow fibers are now commercially available as modules for reverse osmosis. The properties of a module for reverse osmosis are evaluated in terms of the proportion of exclusion of solute and the amount of solvent (water) which passes through the membrane. In this invention, it is preferable to use modules with a high rate of removal suitable for concentration of organic compounds of low molecular weight; moreover, these modules should be permeable by large amounts of water at a relatively low pressure. Module membranes for use in reverse osmosis which are commercially available are exemplified in Table 3.

TABLE 3

| | | Module of Reverse Osmosis | |
|---|---|---|---|
| Firm | Trademark | Raw material of membrane | Form of module |
| Toray | CA | polyamide carboxylic acid | spiral |
| | PEC-1000 | bridged polyether complex membrane | spiral |
| Toyobo | HOLLOSEP | cellulose acetate | hollow fiber |
| Teijin | PBIL, TL | polybenzimidazolone | tube |
| | | polyether amide | tube |
| Nitto Denko | NTR-7100 | polyimide | spiral |
| Dow Chem. | Dowex 4K, 20K | cellulose acetate | hollow fiber |
| | | cellulose acetate | spiral |
| Universal Oil | PA-300 | polyether amide | spiral |
| Products | RC-100 | polyether urea | spiral |
| Dupont | B-9, -10 | aromatic polyamide | hollow fiber |
| System, Inc. | | synthetic macromolecule complex membrane | |
| System Company | NS-200 | sulfonated polyfurfuryl alcohol | spiral |

TABLE 3-continued

| Firm | Trademark | Module of Reverse Osmosis Raw material of membrane | Form of module |
| --- | --- | --- | --- |
| Film Tech | FT-30 | | spiral |
| Rhone poulenc | | sulfonated polysulfone | |
| North Star Research | NS-100 | polyethyleneimine-toluenediisocyanate | tube, spiral |
| | NS-101 | polyethyleneimine-acid chloride | |

The membrane for reverse osmosis to be used in the process of concentration of spergualin-related compounds and their synthetic intermediates according to this invention can be properly selected from among these commercially available products. Of these membranes for reverse osmosis, those that are particularly suitable include the PEC-1000 (Toray Industries, Inc.), Hollosep (Toyobo Co., Ltd.), the NTR-7100 series (Nitto Denko Corporation), etc.

With this kind of reverse osmosis, it is possible to use any of the commercially available apparatus for reverse osmosis in which are incorporated the kinds of modules for reverse osmosis described above for the concentration of spergualin-related compounds and their synthetic intermediates. There is no restriction as to the apparatus to be used provided that the purpose of this invention is achieved. As a rule, the capacity of such apparatus to concentrate substances depends on the effective surface area of the membrane for reverse osmosis, so apparatus with membrane modules with a surface area suitable for the scale of the planned use for this invention can be selected.

When the eluate to be concentrated contains inorganic salt, preferably, desalination is carried out, and after the osmotic pressure arising from the inorganic salt has been lowered, the step of concentration by use of the apparatus for reverse osmosis takes place. For the desalination process, the electrodialysis method described above is most satisfactory. Thus, for the purification of spergualin-related compounds and their synthetic intermediates, it is possible to use electrodialysis for the desalination process and reverse osmosis for the concentration process depending on the purpose in mind, and these can be used separately or in combination one after the other.

EXAMPLES

This invention will be explained in detail by reference to examples and by referring partly to the accompanying drawing wherein FIG. 1 is a graph which shows the test results of the desalination by means of electrodialysis, with time as the axis of abscissas and with electroconductivity and yield as the axis of ordinates, but this invention is not to be taken to be limited to these particular examples.

EXAMPLE 1

Electrodialysis was done in an apparatus for electrodialysis (Microasilyzer [phonetic]G-3, Asahi Chemical Industry Co., Ltd.) equipped with an ion-exchange membrane (Asiplex [phonetic]cartridge AC-110-400, Asahi Chemical Industry Co., Ltd.) with an effective membrane surface area of 400 $cm^2$ with 500 m$\lambda$ of a 1 M NaCl solution that contained 5 g of glyoxylyl-spermidine-2HCl as the sample solution and with 400 m$\lambda$ of tap water as the outer fluid. The salt concentration of the sample solution was monitored in terms of the electroconductivity, mS/cm, of the solution. At the same time, the sample concentration was measured by high-pressure liquid chromatography. The results of the tests are shown in Table 4 and FIG. 1. Desalination was completed in about 60 minutes. By concentration under reduced pressure, 4.95 g of glyoxylylspermidine-2HCl was recovered from the sample solution (yield, 99%).

TABLE 4

| | Microasilyzer G3/AC-110-400 | | |
| --- | --- | --- | --- |
| Time (min) | Electroconductivity (mS/cm) | pH | Yield (%) |
| 0.0 | 85.1 | 6.3 | 100 |
| 10.0 | 72.6 | 6.2 | |
| 20.0 | 48.0 | 6.1 | |
| 30.0 | 22.1 | 6.1 | |
| 40.0 | 10.5 | 6.2 | 100 |
| 50.0 | 7.56 | 6.3 | |
| 60.0 | 6.65 | 6.36 | 99 |

EXAMPLE 2

Electrodialysis was done in an apparatus for electrodialysis (Microasilyzer G-3, Asahi Chemical Industry Co., Ltd.) equipped with an ion-exchange membrane (cartridge AC-110-400, Asahi Chemical Industry Co., Ltd.) with an effective membrane surface area of 400 $cm^2$ with 500 m$\lambda$ of a 1 M NaCl solution that contained 5 g of 15-deoxyspergualin-3HCl as the sample solution and with 400 m$\lambda$ of tap water as the outer fluid. The salt concentration of the sample solution was monitored in terms of the electroconductivity (mS/cm) of the solution. At the same time, the sample concentration was measured by high-pressure liquid chromatography. Desalination was complete in about 60 minutes. By concentration under reduced pressure, 4.7 g of 15-deoxyspergualin-3HCl was recovered from the sample solution (yield, 94%).

EXAMPLE 3

Pressure of 55 kg/$cm^2$ was applied to 60 $\lambda$ of an aqueous solution of 600 g of glyoxylylspermidine-2HCl in an apparatus for reverse osmosis equipped with Hollosep HR 5155 (Toyobo Co., Ltd.). In an operation time of 37 minutes, 50 $\lambda$ of dialyzed liquid was obtained. In this dialyzed liquid, glyoxylvlspermidine was not detected. The concentrated liquid and the washing liquid were pooled, giving 11.5 liters (concentration was 5.2-fold, with 98.3% recovery of glyoxylylspermidine). The volume of dialyzed liquid, the pressure, and the recovery of glyoxylylspermidine-2HCl with time are shown in Table 5.

TABLE 5

| | Concentration of glyoxylylspermidine by reverse osmosis | | | | |
| --- | --- | --- | --- | --- | --- |
| Operation time (min, sec) | Pressure (Kg/$cm^2$) | | Dialyzed fluid | | Yield (%) |
| | $P_1$ | $P_2$ | Flux (l/min) | Total volume (l) | |
| 0 | 55 | 55 | 1.55 | 0 | 100 |
| 7.10 | 55 | 55 | 1.42 | 10 | |
| 14.20 | 55 | 55 | 1.45 | 20 | 99 |
| 21.30 | 55 | 55 | 1.45 | 30 | |
| 29.30 | 55 | 57.5 | 1.40 | 40 | 98.5 |

TABLE 5-continued

| Operation time (min, sec) | Concentration of glyoxylylspermidine by reverse osmosis | | | | |
|---|---|---|---|---|---|
| | Pressure ($Kg/cm^2$) | | Dialyzed fluid | | |
| | $P_1$ | $P_2$ | Flux (l/min) | Total volume (l) | Yield (%) |
| 37.00 | 55 | 55 | 0.82 | 50 | 98.3 |

EXAMPLE 4

A pressure of 55 kg/cm$^2$ was applied to 30 λ of an aqueous solution of 300 g of 15-deoxyspergualin-3HCl in an apparatus for reverse osmosis equipped with Hollosep HR5155 (Toyobo Co., Ltd.). In an operation time of 18 minutes, 25 λ of dialyzed liquid was obtained. In this dialyzed liquid, 15-deoxyspergualin was not detected. The concentration liquid and the washing liquid were pooled, giving 7 liters (concentration was 4.3-fold, with 99% recovery of 15-deoxyspergualin).

EXAMPLE 5

Electrodialysis was done in an apparatus for electrodialysis (Microasilyzer G-3, Asahi Chemical Industry Co., Ltd.) equipped with an ion-exchange membrane (cartridge AC-110-400, Asahi Chemical Industry Co., Ltd.) with an effective surface area of 400 cm$^2$ with 500 mλ of a 1 M NaCl solution that contained 5 g of 15-deoxyspergualin-3HCl as the solution for permeation and with 400 mλ of tap water as the outer fluid. By this procedure, 400 mλ of sample solution was obtained, and this solution was treated by reverse osmosis in a filter device for reverse osmosis equipped with a flat membrane (membrane diameter, 76 mm) of NF-70 Nanofilm (Film Tech) by the application of 15 kg/cm$^2$ pressure by means of N$_2$ gas for filtration. After 70 minutes at this pressure, 320 mλ of dialyzed liquid was obtained, and 80 mλ of concentrated liquid was recovered (concentration was 5-fold, with 93.5% recovery of 15-deoxyspergualin).

This invention thus provides the use of a desalination step by electrodialysis and/or a reverse-osmosis step, by which it is possible to prepare and purify spergualin-related compounds in the highly purified form needed for their use in pharmaceutical preparations, and this invention furthermore provides a means by which such purification can be done efficiently and economically.

The efficiency of this invention is obvious by the fact that it took only 3 days to achieve the processes of desalination and concentration for the manufacture of spergualin-related compounds and their synthetic intermediates in kilogramscale, while by the conventional method that involves concentration by freeze-drying and extraction with organic solvent, it took 13 days.

What we claim is:

1. A process for purification of spergualin-related compounds and their synthetic intermediates, having a molecular weight of 1000 or less comprising subjecting a solution containing a member selected from the group consisting of said compounds and intermediates to a process selected form the group consisting of electrodialysis, reverse osmosis and both electrodialysis and reverse osmosis.

* * * * *